United States Patent [19]

Kusakari et al.

[11] Patent Number: 5,294,550
[45] Date of Patent: Mar. 15, 1994

[54] METHOD OF CULTURING MISHIMA-SAIKO

[75] Inventors: Ken Kusakari; Mineyuki Yokoyama; Mitsuo Yanagi, all of Yokohama, Japan

[73] Assignee: Shiseido Company Ltd., Tokyo, Japan

[21] Appl. No.: 913,884

[22] Filed: Jul. 17, 1992

[30] Foreign Application Priority Data

Jul. 19, 1991 [JP] Japan .................................. 3-179591

[51] Int. Cl.$^5$ .............................. C12N 5/00; C12N 5/02
[52] U.S. Cl. ............................. 435/240.45; 435/240.4; 435/240.48; 435/240.54
[58] Field of Search ........... 435/240.45, 240.4, 240.48, 435/240.54

[56] References Cited

FOREIGN PATENT DOCUMENTS

| | | | |
|---|---|---|---|
| 63-237784 | 10/1988 | Japan .............................. | C12O 5/00 |
| 1-285116 | 11/1989 | Japan .............................. | A01G 1/00 |
| 2-268678 | 11/1990 | Japan . | |
| 2-273131 | 11/1990 | Japan . | |
| 3-232484 | 10/1991 | Japan .............................. | A01H 4/00 |

OTHER PUBLICATIONS

Hiraoka et al., Shoyakugaku Zasshi, 37(1), 62–67, (1983).
Hiraoka et al., Plant Cell Reports, 5(5), 319–321, (1986).
Mlodzianowski, Bull. Soc. Amis. Sci. Letters Poznan, Ser. D-14, 3–6, (1973).
Wilson et al., Botany 3rd Edition, Holt, Rinehart and Winston, p. 332, (1962).
Nippon Nogeikagaku Kaishi (Journal of the Japanese Agricultural Chemistry), Mar. 15, 1989, p. 496. (w/English translation).
Syoyakugaku Zasshi (J. Pharm.) 28(2), p. 152 (1974).
Derwent Abstract No. 84–06743, Po et al., "Production of Saikosaponins by Callus . . . " & Instutute of Botany, Academia Senica, Taipei, China (5 Meet., 71–72) (1982).

*Primary Examiner*—Douglas W. Robinson
*Assistant Examiner*—Maria L. Osoteo
*Attorney, Agent, or Firm*—Wegner, Cantor, Mueller & Player

[57] ABSTRACT

An improved process for the organ cultivation of a Mishima-saiko root is provided. In the cultivation of a Mishima-saiko root, by carrying out the cultivation while regulating the saccharide concentration to be less than 2%, until the adventitious roots have spread out, and optionally adding an additional saccharide, the productivity of saiko-saponin can be enhanced.

5 Claims, No Drawings

METHOD OF CULTURING MISHIMA-SAIKO

BACKGROUND OF THE INVENTION

1. Field of Invention

The present invention relates to a method of culturing an organ of Mishima-saiko, plants belonging to genus Bupleurum using their root as an explant. More specifically, the present invention relates to an improved method of culturing said organ while regulating the concentration of carbohydrate in a medium over a specific culturing period.

2. Description of Related Art

The tissue (or organ) culture of saponincontaining plants for galenical has attracted attention in terms of providing a stable supply of galenical resources. Among these, since ginseng is very expensive, extensive attempts have been made to effectively produce saponin by culturing a callus derived from a root of ginseng, *Panax Schinseng* Nees, or an adventitious root or hairy root thereof.

Saiko (root of Mishima-saiko) is a galenical formulated in a wide variety of Chinese medicines, and has been known to contain as its components saiko-saponin a to d comprised of triterpenoids as genin. From the viewpoint of a stable supply of the galenical resources as described above, attempts also have been made to cultivate the tissue (or organ) of the Mishima-saiko. In the production of a useful substance by tissue (or organ) culture, the contents of the useful substance are generally enhanced by hormone regulation, etc., but in the case of Mishima-saiko, it is difficult to produce saiko-saponin by callus culture (Syoyaku Gaku Zasshi (Society of Galenicals) 28 (2) pp 152–160, 1974).

On the other hand, there was also an attempt made to produce saiko-saponin with Mishima-saiko cultured root. In this case, the production of saponin was enhanced by varying the ratio of nitric ions to ammonium ions as nitrogen sources (Nippon Nogeikagaku Zasshi (Agriculture Society of Japan), 63, 35, page 496, March, 1989)

However, there has been no investigation into the influence of carbohydrates, which are the most essential components among the medium components, upon the production of saponin.

Therefore, the object of this invention is to provide an organ culturing process which enables the effective production of saiko-saponins using root of the Mishima-saiko as the explant of the same.

In the course of the examination of the culture conditions in the culturing process using the root of Mishima-saiko as an explant of same, for example, the influence of various hormones, the present inventors unexpectedly found that the regulation of the carbohydrate concentration to be added to the medium depending on the culturing periods significantly influences the productivity of saiko-saponins, to thereby achieve this invention.

SUMMARY OF THE INVENTION

According to this invention, the above object is achieved by a method of culturing organ of Mishima-saiko, plants belonging to genus Bupleurum, using their root as an explant, which comprises regulating the concentration of the carbohydrate component in a medium to be less than 2%, by weight per total medium, over a specific culturing period wherein the lateral roots are fully spread out.

According to the present invention, an improved method is provided by regulating the carbohydrate concentration to a level less than a specific level for a specific culturing period of initial culturing, in the production of saiko-saponin by the culture of the root of Mishima-saiko. In particular, when the concentration of carbohydrate is regulated to be less than 2%, by weight per total medium, until the lateral roots are fully spread out, and an appropriate amount of carbohydrate is added to the medium, the productivity of saiko-saponin can be enhanced.

DESCRIPTION OF THE PREFERRED EMBODIMENT

The "Mishima-saiko" used in this invention is a plant belonging to the genus *Bupleurum*, and *Bupleurum falcatum* L, *B. chinese* DC, *B. komarovianum* Lincz, and *B.scorzoneraefolium* Wild can be mentioned as preferable ones. In particular, *Bupleurum falcatum* L is preferred. In the culture, the root is used as the explant. Any roots such as regenerated roots from callus, roots harvested from the plant, and hairy roots induced by infection with *Acrobacterium rhizogenes* can be used as such a root. Of these, generated roots originating in the callus are preferably used. The root thus prepared is sterilized in a conventional manner, as occasion demands, and then used in the culture according to this invention.

The medium that can be used is one suitable for producing a useful substance by the culture of organ and comprised of macro-essential elements and microessential elements, as well as water, inorganic salts, carbohydrates, and if necessary, growth regulators such as auxins, e.g., indole-3-acetic acid (IAA), indole-3-butyric acid (IBA), etc., and cytokinins.

More specifically, a Murashige-Skoog medium, Linsmeier-Skoog medium, White medium, Gamborg medium (B5 medium), Nitsch medium, Heller medium, and modified media having basic composition according to these modified media and having the content of carbohydrates restricted to prescribed amounts, can be mentioned. In these media, sucrose is utilized as a carbohydrates source as a rule, and glucose or fructose may be used as another carbohydrates source, in a concentration of 2–3%, by weight per total medium. In the case of the present invention, the concentration of the carbohydrate as the medium component is regulated to be less than 2%, by weight per total medium, for the culturing period until the lateral roots are fully spread out. As the regulation method, it is simple and convenient to add the carbohydrate all at once at the initiation of the cultivation so that the concentration of the carbohydrate is less than 2%, by weight per total medium, but the carbohydrate may be added in several portions while regulating the concentration of carbohydrate to be less than 2%, by weight per total medium.

In the present invention, the phrase "the roots of Mishima-saiko are fully spread out" refers to the state wherein the number of the lateral roots are no longer substantially increased even by further culturing. Consequently, in the production of saiko-saponin according to the present invention, the concentration of carbohydrate in the medium after the above-mentioned lateral roots have already spread out (i.e., the stage where the lateral roots are growing, and the stages thereafter) may not be regulated to be less than 2%, by weight per total medium. The present inventors have confirmed that a high yield of saiko-saponin can be realized by periodically or continuously adding a carbohydrate, particularly sucrose, so that the carbohydrate concentration after the above-mentioned period is more than 2%, by weight per total medium. Similar results were obtained in the case where glucose or fructose was used instead of sucrose. Besides the addition of sucrose, the concentration of carbohydrate may be regulated by exchanging the whole medium for a fresh one.

The above culture may be carried out using a liquid medium or an agar solid medium at a temperature between 20° C. and 30° C. with irradiation of light, a dark place, or under alternative light and dark conditions.

According to the culturing process of the present invention, by regulating the carbohydrate concentration at a constant level for the period wherein the lateral roots of Mishima-saiko are fully spread out, the absolute amounts of saiko-saponins to be produced can be enhanced. The term "to enhance the absolute amount" indicates "to increase the product of the dry weight of cultured root after the culture by the content of saiko-saponin".

The effect of the present invention can be confirmed by quantitatively measuring the saiko-saponins extracted from the cultured root with a lower alcohol, e.g., methanol, ethanol, isopropanol, or n-butanol, watercontaining alcohol thereof, or an extractant having an alkali added thereto by high performance liquid chromatography (HPLC).

According to this invention, the lateral roots of Mishima-saiko are fully spread out within about two weeks, for example, where the concentration is restricted to 1% by weight per total medium, comparison with a conventional process which utilizes a B5 medium and regulates the initial sucrose concentration to 2–4%, by weight per total medium. Although the dry weights of the root per se are not thought to show any difference in these two cases, the content of saiko-saponin per dry weight was significantly enhanced. Concerning the merit of the lower concentration of the carbohydrate, the present invention also gives a good result regarding the final production amount when the culture is further continued, for the inherent saiko-saponin production by the culturing. Where the culture is continued, it has been found that, contrary to the initial cultivation, additional carbohydrates may be advantageously added to the medium while continuing the culture, to thereby achieve a higher carbohydrate concentration (for example about 3–6%). For example, in the culture of the root of Mishima-saiko using a medium containing a total carbohydrate concentration of 4%, where the whole amount of carbohydrate is added at the initial stage and the culture is totally carried out for 6 weeks, compared with the culturing where the carbohydrate concentration is regulated to be about 1%, by weight per medium, for the culturing period until the lateral roots are fully spread out, and the remaining carbohydrate are added at the stage where the lateral roots have already spread out (two weeks after the initiation of the culture), the culture is continued for the same period. According to this comparison, although no substantial difference can be seen between the two cases concerning the dry weight of the cultured root, the content of saiko-saponins in the latter case amounts to twice that of the former case. When carrying out the latter process, good results can be obtained if the remaining carbohydrates are added in several portions.

EXAMPLES

The following examples only illustrate the invention, and should not be interpreted as a limitation thereof.

EXAMPLE 1

The seeds of *Bupleurum falcatum* L. were soaked in 70% alcohol for 30 seconds, followed by soaking a sodium hypochroide for 30 minutes to carry out the sterilization. After being washed with sterilized water, the seeds were allowed to germinate in a Linsmeier-Skoog medium (LS medium) immobilized with 1% agar. The roots of the plant bodies thus sterilizably grown were cut off, and cultured on an LS solid medium containing 0.1 mg/l of IBA. As a result, the propagation of callus was seen, and the differentiation of adventitious roots was observed from the resulting callus. The adventitious roots were cut off, administrated in B5 liquid medium containing 3 mg/l of IBA, and the subculture was carried out in a dark place at 110 rmp every month. After the subculture, 1 g of root (green weight) at about 3 weeks was planted into a 500 ml volume conical flask charged with 200 ml of sterilized a modified B5 medium, for example, as described below.

| Modified B5 medium mg/l: | |
|---|---|
| KNO$_3$ | 2500 |
| (NH$_4$)$_2$SO$_4$ | 134 |
| NaH$_2$PO$_4$.H$_2$O | 150 |
| CaCl$_2$.2H$_2$O | 150 |
| MgSO$_4$.7H$_2$O | 250 |
| FeSO$_4$.7H$_2$O | 27.8 |
| Na$_2$EDTA | 37.3 |
| MnSO$_4$.H$_2$O | 10 |
| ZnSO$_4$.7H$_2$O | 2.0 |
| H$_3$BO$_3$ | 3.0 |
| CuSO$_4$.5H$_2$O | 0.025 |
| Na$_2$MoO$_4$.2H$_2$O | 0.25 |
| KI | 0.75 |
| CoCl$_2$.6H$_2$O | 0.025 |
| Myo-inositol | 100 |
| Thiamine.HCl | 10 |
| Pyridoxine.HCl | 1 |
| Nicotinic acid | 1 |
| IBA | 8 |
| Sucrose | contents as described below |

The sucrose concentration of each medium was regulated to be 1, 2, or 4%, and the culture was carried out at 23° C. for 2 to 6 weeks in a dark place while shaking at 100 rpm. The sample collected at each culturing period was freeze-dried, and then an extraction from 100 mg of dry weight with 3 ml of 75% methanol containing 5% KOH was carried out twice. The extract was concentrated to dryness by a rotary evaporator, then dissolved in a certain amount of 75% alcohol, and the saiko-saponins a and d were quantitatively determined (CAPCELL PAK C$_{18}$; acetonitrile/water=40/60 UV 210 nm, 1 ml/min).

The content (%) of saiko-saponin (a+d) for each dry root, the dry weight (g) per 1 l of the medium, and the productivity of saiko-saponins (a+d, mg/l) were as shown in Table 1.

TABLE 1

| Sucrose Concentration (%) | Culturing period (week) | A Content of saponin (a + d) (% based on dry weight) | B Dry weight (g per l of medium) | A × B × 10 Productivity of saponin (mg per l of medium) |
| --- | --- | --- | --- | --- |
| 1 | 2 | 0.111 | 4.93 | 5.5 |
|   | 3 | 0.286 | 6.09 | 17.4 |
|   | 4 | 0.372 | 6.19 | 23.0 |
|   | 5 | 0.364 | 6.33 | 23.0 |
|   | 6 | 0.393 | 5.66 | 22.2 |
| 2 | 2 | 0.080 | 5.06 | 4.0 |
|   | 3 | 0.177 | 7.99 | 14.1 |
|   | 4 | 0.369 | 11.16 | 41.2 |
|   | 5 | 0.442 | 12.39 | 54.8 |
|   | 6 | 0.743 | 10.89 | 80.9 |
| 4 | 2 | 0.085 | 4.13 | 3.5 |
|   | 3 | 0.104 | 7.16 | 7.5 |
|   | 4 | 0.218 | 12.49 | 27.2 |
|   | 5 | 0.418 | 19.65 | 82.1 |
|   | 6 | 0.716 | 21.84 | 156 |

From the above results, the amount of production of saponin 2 to 3 weeks after the culture was at maximum with a sucrose concentration of 1%. (Also, in the culture after 3 weeks, the saponin production was much lower than in the other cases, due to the lack of carbohydrate source).

EXAMPLE 2

The initial sucrose concentration was defined to 0.5, 1, 1.5, 2.0, 3.0, and 4.0% and the remaining carbohydrate was added to be 4% of the total amount of carbohydrate added (50% sucrose aqueous solution, filter sterilized), and Mishima-saiko was cultured as described in Example 1. The productivity of the sum of saiko-saponins a and d per l of medium [=the content (%) of saiko-saponin (a+d) per for dry root×dry weight (g) per 1 l of the medium) was as shown in Table 2.

TABLE 2

|   | Initial sucrose Concentration (%) | | | | | |
| --- | --- | --- | --- | --- | --- | --- |
|   | 0.5 | 1 | 1.5 | 2.0 | 3.0 | 4.0 |
| Saponin productivity (a + d, mg/l) | 328 | 326 | 301 | 270 | 192 | 177 |

Cultured for 6 weeks

It can be understood from these results that a high saponin productivity can be obtained where the initial sucrose concentration is regulated to be less than 2% by weight per total medium.

EXAMPLE 3

The roots of Mishima-saiko were cultured as described in Example 1, except that either the sucrose concentration was regulated to be 4, 5, 6, 7, 8, or 9%, by weight per total medium, at the initiation of the culture, or the culture was carried out for 2 weeks at the initial sucrose concentration of 1%, by weight per total medium, and immediately thereafter, an amount of sucrose corresponding to 3, 4, 5, or 6%, by weight per total medium, was added. The productivity of the sum of saiko-saponins a and d was as shown in Table 3.

TABLE 3

| Amount of total sucrose (%) | 4 | 5 | 6 | 7 | 8 | 9 |
| --- | --- | --- | --- | --- | --- | --- |
| Example: after cultured for 2 weeks at 1%, the remaining amount was added all at once. | 372 | 385 | 561 | 605 | 600 | 501 |
| Comparative Example: Total amount was added at all one at the initial culture. | 162 | 90 | 56 | 10 | 3 | 1 |

As described above, after the lateral roots were derived, even when the sucrose concentration was regulated to a considerably high level, the productivity of saponins could be enhanced without an adversely affect thereon.

Note: The procedures as described in Example 3 are repeated, except that glucose, and a mixture of sucrose and glucose are used instead of sucrose, to give the same results as that of Example 3.

EXAMPLE 4

The culture of Example 1 was repeated for 6 weeks, except that the culture was carried out for 2 weeks with the initial sucrose concentration being regulated to be 1%, by weight per total medium, and then an amount of sucrose corresponding to 1%, by weight per total medium, was added three times at 5 day intervals. For comparison, a similar culture was carried out for 6 weeks with the initial sucrose concentration being regulated to be 4% by weight per total medium.

| Former (Example) | 305 mg/l |
| --- | --- |
| Latter (Comparative Example) | 162 mg/l |

From these results it was proven that, in the production of saiko-saponin by the culture of the root of Mishima-saiko, the additional saccharide also may be added in several portions, after the saccharide concentration in the medium is regulated to a level of less than a specific level, until the lateral roots have spread out.

We claim:

1. A process for producing saponin comprising the steps of:
   a) culturing Mishima-saiko root as an explant in a medium having a carbohydrate concentration less than 2% by weight of the total medium for a time sufficient to effect a maximum number of lateral roots and produce saponin;
   b) further culturing the Mishima-saiko root in a medium regulated at a carbohydrate concentration of at least 2% by weight of the total medium to produce saponin; and
   c) recovering the saponin.

2. The method of claim 1 wherein the time of the culturing of step (a) is about two weeks and the carbohydrate concentration in culturing step (b) is about 4–10% by weight of the total medium.

3. A method according to claim 1, wherein said Mishima-saiko is a plant belonging to *Bupleurum falcatum* L.

4. A method according to claim 1, wherein said carbohydrate is sucrose and/or glucose.

5. A method according to claim 1, wherein the carbohydrate is sucrose and/or glucose.

* * * * *